United States Patent [19]

Horodysky et al.

[11] 4,402,842

[45] Sep. 6, 1983

[54] FRICTION REDUCING ADDITIVES AND COMPOSITIONS THEREOF

[75] Inventors: Andrew G. Horodysky, Cherry Hill; Joan M. Kaminski, Mullica Hill, both of N.J.

[73] Assignee: Mobil Oil Corporation, New York, N.Y.

[21] Appl. No.: 291,005

[22] Filed: Aug. 7, 1981

[51] Int. Cl.$^3$ .............................................. C10M 1/38
[52] U.S. Cl. ...................... 252/47.5; 44/53; 44/73; 252/47; 564/501; 564/511; 564/512
[58] Field of Search ....................... 252/47, 475; 44/53, 44/73; 564/501, 511, 512

[56] References Cited

U.S. PATENT DOCUMENTS

| 2,281,521 | 4/1942 | Fuller | 252/47 |
| 2,290,316 | 7/1942 | Cook | 252/47 |
| 2,528,092 | 10/1950 | Smith et al. | 252/47.5 X |
| 2,703,784 | 3/1955 | Fields | 252/47.5 X |
| 2,763,616 | 9/1956 | Brooks | 252/47.5 |
| 2,971,909 | 2/1961 | Fields | 252/47.5 X |
| 3,399,041 | 8/1968 | McCabe | 252/47.5 X |

FOREIGN PATENT DOCUMENTS 811860  4/1959  United Kingdom ............... 252/47.5

Primary Examiner—Andrew Metz
Attorney, Agent, or Firm—Alexander J. McKillop; Michael G. Gilman; Claude E. Setliff

[57] ABSTRACT

The invention provides products of reaction formed by reacting an amine, a mercaptan and an aldehyde. The invention also provides liquid fuel and lubricant compositions.

25 Claims, No Drawings

FRICTION REDUCING ADDITIVES AND COMPOSITIONS THEREOF

BACKGROUND OF THE INVENTION

1. Field of the Invention

This invention relates to lubricant and fuel additives and compositions thereof and, more particularly, to liquid fuel and lubricant compositions comprising fuels or oils of lubricating viscosity or greases prepared therefrom containing a minor friction reducing amount of products made by reacting together an amine, an aldehyde and a mercaptan.

2. Description of the Prior Art

Many means have been employed to reduce overall friction in modern engines, particularly automobile engines. The primary reasons are to reduce engine wear thereby prolonging engine life and to reduce the amount of fuel consumed by the engine thereby reducing the engine's energy requirements or fuel consumption. While it is commonly understood that lubricants by definition, reduce friction between moving surfaces, friction reducing additives are agents which when added to lubricants in minor amounts significantly enhance the frictional properties of those lubricants without modifying other physical properties such as viscosity, density, pour point, and the like.

Many of the solutions to reducing fuel consumption have been strictly mechanical, as for example, setting the engines for a leaner burn or building smaller cars and smaller engines. However, considerable work has been with lubricating oils, mineral and synthetic, to enhance their friction or antioxidant properties by modifying them with friction reducing additives.

Although amines and other nitrogen-containing compositions have been added to lubricants for various purposes, the reaction products of this invention are, to applicants' best knowledge, novel, and they have no prior history of use in lubricating compositions as friction reducing additives or in the multifunctional additive areas of anti-corrosion, especially copper corrosion inhibiting, anti-wear or anti-oxidation.

No art is known which teaches or suggests the invention described herein.

SUMMARY OF THE INVENTION

In accordance with the invention, there is provided a product of reaction produced by reacting an amine with a mercaptan and an aldehyde. Also provided is a liquid fuel or a lubricant composition containing same. The lubricant comprises oils of lubricating viscosity or greases therefrom and the liquid fuel comprises liquid hydrocarbon fuels such as gasoline, fuel oil, and the like, as well as alcohol fuels, such as methanol and ethanol, or mixtures thereof.

DESCRIPTION OF SPECIFIC EMBODIMENTS

The amines useful in this invention include hydrocarbyl mono- and diamines, wherein the hydrocarbyl portion, which can be alkyl, alkenyl, cycloalkyl, cycloalkenyl, alkaryl or aralkyl, may contain from 10 to 30 carbon atoms. Among the amines that are useful in the practice of this invention may be included cocoamine, decylamine, dodecylamine, tetradecylamine, oleylamine, isostearylamine, myristylamine, palmitylamine, stearylamine, N-oleyl-1,3-propylenediamine, and N-coco-1,3-propylenediamine.

Also included are the polyalkylene polyamines of the formula $$RNH(R^1NH)_xH$$

wherein R is H or a $C_1$ to $C_{20}$ hydrocarbyl group, $R^1$ is a $C_2$ to $C_5$ alkylene group and x is 1 to 10. Some specific members are ethylenediamine, N-oleyl-ethylenediamine, N-oleyl-propylenediamine, N-coco-triethylene tetramine, diethylene triamine, tetraethylene pentamine, and the like.

The reaction product is prepared by reacting the amine with an aldehyde of the formula $$R^2CHO$$

wherein $R^2$ is H or a $C_1$ to $C_8$ hydrocarbyl group (e.g., alkyl, alkenyl, cycloalkyl or aralkyl) and a mercaptan of the formula $$R^3SH$$

wherein $R^3$ is a $C_8$ to $C_{30}$ hydrocarbyl group, preferably an alkyl group. $R^3$ can be a straight chain or branched chain, with the straight chain mercaptans being preferred.

The useful aldehydes, of which formaldehyde and paraformaldehyde are preferred, include acetaldehyde, propionaldehyde, butyroaldehyde and 2-ethylhexyl aldehyde.

Preferred among the useful mercaptans is n-dodecyl mercaptan. Others that may be used include n-nonyl, n-octyl, n-decyl, n-myristyl, n-hexadecyl, stearyl, and oleyl mercaptan.

The following formula depicts the structure of a product that may be present, at least to some extent, in the reaction product:

$$RNHCHSR^3 \atop {|\atop R^2}$$

Another possible structure may be:

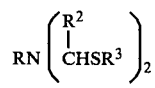

$$RN\left(\begin{array}{c}R^2\\|\\CHSR^3\end{array}\right)_2$$

Since the products are mixtures of compounds, they will be referred to herein as "reaction products" or "products of reaction" or an equivalent expression.

These reaction products can be prepared by refluxing amine, aldehyde, and mercaptan at a ratio of from about 1:1:0.5 to about 1:1:1, respectively, in either polar or non-polar solvents such as n-butanol, isopropanol, toluene, or benzene until an expected amount of H₂O is removed. A temperature of from about 80° C. to about 160° C. can be used but from about 110° C. to about 140° C. is preferred.

Alternatively, the Mannich base can be prepared by reacting equimolar amounts of amine and aldehyde in an alcoholic solvent until an expected amount of H₂O is removed. The reaction is run for about 1 to 4 hours between about 80° and 145° C. Then, an equimolar amount, for example, of mercaptan may be added and reacted for about 3 to 6 hours at from about 110° C. to about 160° C.

In general, in most instances, the product is employed in an amount from about 0.1% to about 10% by weight, and preferably in an amount of from about 0.5% to about 5% by weight of the total weight of the composition. When used in hydrocarbon or alcoholic fuels, they may be present to the extent of from about 0.00001 to about 1% by weight, preferably from about 0.001 to about 0.01% by weight.

Of particular significance is the ability to counteract the accelerating effect of oxidation on metal and lubricant deterioration achieved by employing the aforementioned product. Thus, these products may be incorporated in liquid hydrocarbon fuels or in lubricating media which may comprise liquid hydrocarbon oils in the form of either a mineral oil or a synthetic oil, or mixtures thereof, or in the form of a grease, in which any of the aforementioned oils are employed as a vehicle. These can also contain detergents and dispersants, as well as antioxidants, inhibitors, antiwear, extreme pressure, antifoam, pour depressant, and viscosity index improving additives without negating the beneficial properties of the novel compositions of this invention. The compositions can include commonly used additives such as phenates, sulfonates, polymers, metal dithiophosphates, succinimides, and the like. In general, mineral oils employed as the lubricant or grease vehicle may be of any suitable lubricating viscosity range as, for example, from about 45 SSU at 100° F. to about 6,000 SSU at 100° F., and preferably from about 50 SSU at 210° F. to about 250 SSU at 210° F. These oils may have viscosity indexes varying from below 0 to about 100 or higher. Viscosity indexes from about 70 to about 95 are preferred. The average molecular weights of these oils may range from about 250 to 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, di(-butylphthalate) fluorocarbons, silicate esters, silanes, esters of phosphorous-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl) ether, phenoxy phenylethers, etc.

The lubricating vehicles of the aforementioned greases of the present invention, containing the above-described products, are combined with a grease-forming quantity of a thickening agent. For this purpose, a wide variety of material may be employed. These thickening or gelling agents may include any of the conventional metal salts or soaps, which are dispersed in the lubricating vehicle in grease-forming quantities, in such degree as to impart to the resulting grease composition the desired consistency. Other thickening agents that may be employed in the grease formation may comprise the non-soap thickeners, such as surface modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming greases, can be used in preparing the aforementioned improved greases in accordance with the present invention.

The following Examples will specifically illustrate the invention. It will be understood that they are meant to be illustrations of and not limitations to the invention.

EXAMPLE 1

Reaction Product of Oleylamine, Formaldehyde, and Dodecyl Mercaptan

A mixture of oleylamine (200 g), 95% formaldehyde (23.7 g), and n-dodecyl mercaptan (151 g) was refluxed in 175 cc toluene. The expected amount of water was removed by azeotropic distillation. The reaction temperature was raised to 135° C., and no additional water formed. Toluene was removed by high speed rotary evaporation, and the product residue was filtered through diatomaceous earth. The product solidified to an off-white waxy solid at room temperature. The infrared spectrum contained no characteristic carbon nitrogen double bond absorption at 1010 and 910 cm$^{-1}$.

EXAMPLE 2

Reaction Product of N-Oleyl-1,3-Propylenediamine, Formaldehyde, and Dodecyl Mercaptan A mixture of N-oleyl-1,3-propylenediamine (104 g), 95% formaldehyde (10.2 g), and n-dodecyl mercaptan (64.6 g), was refluxed in 80 cc toluene. The expected amount of water was recovered by azeotropic distillation. The reaction temperature was raised to 130° C., and no additional water formed. Toluene was removed by high speed rotary evaporation. The product was filtered through diatomaceous earth yielding a clear, brown fluid.

EXAMPLE 3

Reaction Product of Cocoamine, Formaldehyde, and Dodecyl Mercaptan

A mixture of cocoamine (79 g), 95% formaldehyde (12.5 g), and n-butanol solvent (80 g) was refluxed until water no longer distilled over. The reaction solution was cooled to room temperature, and n-dodecyl mercaptan (73 g) was added in bulk. The reaction was allowed to reflux at 120° C. for 3½ hours. The solvent was removed by high speed rotary evaporation, and the product residue was filtered through diatomaceous earth. The infrared spectrum of the resulting off-white waxy solid contained no characteristic carbon nitrogen double bond absorption at 1010 and 910 cm$^{-1}$, indicating formation of the Mannich base rather than Schiff's base type product.

EXAMPLE 4

Reaction Product of Ethylenediamine, Formaldehyde, and n-Dodecyl Mercaptan

Approximately 60 g of ethylenediamine was added at room temperature to a solution of n-dodecyl mercaptan (101.2 g) and 95% formaldehyde (15.8 g) in 240 cc toluene. Water was removed by azeotropic distillation. Then solvent and excess ethylenediamine were removed by vacuum distillation (165° C., 2 mm Hg). The product was filtered hot through diatomaceous earth and immediately crystallized to an off-white waxy solid.

EVALUATION OF THE PRODUCTS

The reaction products derived from the reaction of oleylamine, cocoamine, N-oleyl-1,3-propylene diamine, and ethylenediamine with formaldehyde and mercaptan were blended into a fully formulated engine oil (SAE 5W-20) containing an inhibitor package which includes detergent and dispersant and tested on the Low Velocity Friction Apparatus (LVFA).

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam-motor arrangement.

Procedure

The rubbing surfaces and 12–13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant.

Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of oil plus additive})}{(U_k \text{ of oil alone})} \times 100$$

Thus, the value for the oil alone would be zero for the form of the data used in the Table below.

TABLE 1

| | Friction Characteristics | | |
|---|---|---|---|
| | Additive Conc. | Reduction or % Change in Coefficient of Friction | |
| Example No. | Wt. % | 5 Ft./Min. | 30 Ft./Min. |
| Base Oil (fully formulated engine oil containing detergent, dispersant, inhibitor package) | — | 0 | 0 |
| Example 1 Reaction product of oleylamine, formaldehyde and dodecyl mercaptan | 4<br>2 | 28<br>18 | 24<br>23 |
| Example 2 Reaction product of N—oleyl-1,3-propylene-diamine, formaldehyde, and dodecyl mercaptan | 4 | | 14 |
| Example 3 Reaction product of cocoamine, formaldehyde, and dodecyl mercaptan | 4 | 22 | 28 |
| Example 4 Reaction product of ethylenediamine, formaldehyde and dodecyl mercaptan | 4 | | 15 |

From the the data it can readily be seen that friction was reduced significantly relative to the base oil with a maximum reduction of 28% in the coefficient of friction. Even with the use of only 2% of the oleyl derivative (see Example 1), the coefficient of friction was reduced by 18% to 23%.

The products were also evaluated for oxidation stability. In most cases, improvements in oxidative stability over the base oil were observed. Basically, the test lubricant is subjected to a stream of air which is bubbled through at the rate of 5 liters per hour at 425° F. for 24 hours. Present in the composition are samples of metals commonly used in engine construction, namely, iron, copper, aluminum, and lead. See U.S. Pat. No. 3,682,980, incorporated herein by reference, for further details of the test. Improvements in viscosity index or neutralization number (or both) show effective control. See results in Table 2. As shown by these criteria, the additives were rated good.

TABLE 2

| | Catalytic Oxidation Test 40 hours @ 325° F. | | |
|---|---|---|---|
| | Additive Conc. Wt. % | % Inc. in Visc. of Oxidized Oil Using KV @100° F. | Neutral Number |
| Base Oil - 0% Additive 200" Solvent Paraffin Neutral Lubricating Oil | — | 67 | 3.62 |
| Example 1 Reaction product of oleylamine, formaldehyde, and dodecyl mercaptan | 3<br>1 | 13<br>23 | 2.85<br>4.03 |
| Example 2 Reaction product of N—oleyl-1,3-propylene-diamine, formaldehyde, and dodecyl mercaptan | 3<br>1 | 9<br>12 | 1.66<br>2.5 |
| Example 3 Reaction product of cocoamine, formaldehyde, and dodecyl mercaptan | 3<br>1 | 14<br>13 | 2.72<br>3.06 |
| Example 4 | | | |

TABLE 2-continued

| | Catalytic Oxidation Test 40 hours @ 325° F. | | |
|---|---|---|---|
| | Additive Conc. Wt. % | % Inc. in Visc. of Oxidized Oil Using KV @100° F. | Neutral Number |
| Reaction product of ethylenediamine, formaldehyde, and dodecyl mercaptan | 3 | 9 | 1.35 |
| | 1 | 13 | 1.94 |

Also, copper strip corrosion tests were run in accordance with ASTM D130-80, the results of which are shown in Table 3. Effective corrosion inhibition was observed.

TABLE 3

| Copper Strip Corrosivity Characteristics | | | |
|---|---|---|---|
| | Conc. in 200" SPN | ASTM D130-80 250° F., 3 Hrs. | ASTM D130-80 210° F., 6 Hrs. |
| Example 1 Reaction product of oleylamine, formaldehyde, and dodecyl mercaptan | 3 1 | 1B 1B | 1B 1B |
| Example 2 Reaction product of N—oleyl-1,3-propylene-diamine, formaldehyde, and dodecyl mercaptan | 3 1 | 1A 1A | 1B 1B |
| Example 3 Reaction product of cocoamine, formaldehyde, and dodecyl mercaptan | 3 1 | 1A 1A | 1B 1A |
| Example 4 Reaction product of ethylenediamine, formaldehyde, and dodecyl mercaptan | 3 1 | 1B 1B | 1B 1B |

We claim:

1. A reaction product produced by reacting an alkyl, alkenyl, cycloalkyl or cycloalkenyl mono or diamine having 10 to 30 carbon atoms or a polyamine of the formula $$RNH(R^1NH)_xH$$

wherein R is hydrogen or a $C_1$ to $C_{20}$ alkyl or alkenyl group, $R^1$ is a $C_2$ to $C_5$ alkylene group and x is 1 to 10, with a mercaptan having the formula $$R^3SH$$

wherein $R^3$ is a hydrocarbyl group containing from 8 to 30 carbon atoms and an aldehyde of the formula $$R^2CHO$$

wherein $R^2$ is hydrogen or a $C_1$ to $C_8$ alkyl group, the reaction employing the respective reactants in molar ratios of from about 1:0.5:1 to about 1:1:1 and temperatures of from about 80° C. to about 160° C.

2. The reaction product of claim 1 wherein the mercaptan is dodecyl mercaptan.

3. The reaction product of claim 1 wherein the aldehyde is formaldehyde.

4. The reaction product of claim 1 wherein the amine is oleylamine, N-oleyl-1,3-propylenediamine, cocoamine or ethylenediamine.

5. The reaction product of claim 1 wherein the amine is oleylamine, the aldehyde is formaldehyde and the mercaptan is dodecyl mercaptan.

6. The reaction product of claim 1 wherein the amine is N-oleyl-1,3-propylenediamine, the aldehyde is formaldehyde and the mercaptan is dodecyl mercaptan.

7. The reaction product of claim 1 wherein the amine is cocoamine, the aldehyde is formaldehyde and the mercaptan is dodecyl mercaptan.

8. The reaction product of claim 1 wherein the amine is ethylenediamine, the aldehyde is formaldehyde and the mercaptan is dodecyl mercaptan.

9. A composition comprising a major proportion of an oil of lubricating viscosity, greases prepared from oils of lubricating viscosity, liquid hydrocarbon fuels, alcoholic fuels or mixtures of such fuels and an antifriction amount of the reaction product produced by reacting an alkyl, alkenyl, cycloalkyl or cycloalkenyl mono- or diamine having 10 to 30 carbon atoms or a polyalkylene-polyamine of the formula $$RNH(R^1NH)xH$$

wherein R is hydrogen or a $C_1$ to $C_{20}$ alkyl or alkenyl group, $R^1$ is a $C_2$ to $C_5$ alkenyl group and x is 1 to 10, with a mercaptan having the formula $$R^3SH$$

wherein $R^3$ is a hydrocarbyl group containing from 8 to 30 carbon atoms and an aldehyde having the formula $$R^2CHO$$

wherein $R^2$ is hydrogen or a $C_1$ to $C_8$ alkyl group, the reaction employing the respective reactants in molar ratios of from about 1:0.5:1 to about 1:1:1 and temperatures of from about 80° C. to about 160° C.

10. The composition of claim 9 wherein in preparing the reaction product, the mercaptan used is dodecyl mercaptan.

11. The composition of claim 9 wherein in preparing the reaction product, the aldehyde used is formaldehyde.

12. The composition of claim 9 wherein in preparing the reaction product, the amine is oleylamine, N-oleyl-1,3-propylenediamine, cocoamine or ethylenediamine.

13. The composition of claim 9 wherein in preparing the reaction product, the amine, aldehyde and mercaptan used are, respectively, oleylamine, formaldehyde and dodecyl mercaptan.

14. The composition of claim 9 wherein in preparing the reaction product, the amine, aldehyde and mercaptan used are, respectively, N-oleyl-1,3-propylenediamine, formaldehyde and dodecyl mercaptan.

15. The composition of claim 9 wherein in preparing the reaction product, the amine, aldehyde and mercaptan used are, respectively, cocoamine, formaldehyde and dodecyl mercaptan.

16. The composition of claim 9 wherein in preparing the reaction product, the amine, aldehyde and mercaptan used are, respectively, ethylenediamine, formaldehyde and dodecyl mercaptan.

17. The composition of claim 9 wherein the lubricant is a mineral oil, a synthetic oil, mixtures of such oils or a grease made from any of them.

18. The composition of claim 17 wherein the lubricant is a mineral oil.

19. The composition of claim 17 wherein the lubricant is a synthetic oil.

20. The composition of claim 17 wherein the lubricant is a mixture of synthetic and mineral oils.

21. The composition of claim 17 wherein the lubricant is a grease.

22. The composition of claim 12 wherein the liquid fuel is a liquid hydrocarbon or alcohol fuel, or mixtures thereof.

23. The composition of claim 22 wherein the liquid hydrocarbon fuel is gasoline or fuel oil.

24. The composition of claim 22 wherein the alcohol fuel is ethanol or methanol.

25. The composition of claim 22 wherein the fuel is a mixture of the liquid hydrocarbon fuel and alcohol fuel.

* * * * *